(12) United States Patent
Naylor et al.

(10) Patent No.: US 10,414,578 B2
(45) Date of Patent: Sep. 17, 2019

(54) ACTUATOR FOR A PACKAGE AND METHOD OF USE

(71) Applicant: Insys Development Company, Inc., Chandler, AZ (US)

(72) Inventors: Ethan R. Naylor, Silver Spring, MD (US); Lien-Lung Sheu, Chandler, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

(21) Appl. No.: 15/988,118

(22) Filed: May 24, 2018

(65) Prior Publication Data

US 2018/0339842 A1 Nov. 29, 2018

Related U.S. Application Data

(60) Provisional application No. 62/510,822, filed on May 25, 2017.

(51) Int. Cl.
*B65D 83/20* (2006.01)
*B65D 83/30* (2006.01)
*A61K 9/00* (2006.01)
*A61K 31/4468* (2006.01)
*B05B 11/00* (2006.01)
*B05B 11/02* (2006.01)

(52) U.S. Cl.
CPC .......... *B65D 83/206* (2013.01); *A61K 9/0056* (2013.01); *A61K 31/4468* (2013.01); *B05B 11/0054* (2013.01); *B05B 11/02* (2013.01); *B65D 83/30* (2013.01); *A61K 9/006* (2013.01)

(58) Field of Classification Search
CPC . B65D 83/206; A61K 9/0056; A61K 31/4468
USPC .................................. 222/153.13, 325–327; 128/200.14–200.23
See application file for complete search history.

(56) References Cited

U.S. PATENT DOCUMENTS

| 6,527,144 | B2 * | 3/2003 | Ritsche ............... | B05B 11/3011 222/162 |
| 7,726,519 | B2 * | 6/2010 | Heldt ..................... | B05B 11/02 222/153.13 |
| 8,056,765 | B2 * | 11/2011 | Auerbach ........... | B05B 11/3059 222/162 |
| 8,511,515 | B2 * | 8/2013 | Lemaner ............. | A61M 15/009 222/162 |
| 9,156,048 | B2 * | 10/2015 | Le Maner .......... | A61M 15/009 |
| 2007/0164049 | A1 * | 7/2007 | Bonney ............... | B05B 11/3056 222/162 |
| 2011/0163115 | A1 * | 7/2011 | Chen .................. | B05C 17/0103 222/1 |

(Continued)

*Primary Examiner* — Vishal Pancholi
(74) *Attorney, Agent, or Firm* — Wood, Phillips, Katz, Clark & Mortimer (57) ABSTRACT

An actuator for operatively engaging and dispensing a fluent medicament from a package in the form of a spray. The actuator includes a housing to receive and hold the package and further includes a force amplification mechanism that is connected to, and movable with respect to, the housing. The housing further includes a force transfer mechanism operatively engaged with a portion of the package. The force amplification mechanism is coupled with force transfer mechanism for accumulating a force sufficient to dispense the medicament from the package in the form of a spray.

10 Claims, 7 Drawing Sheets

(56) References Cited

U.S. PATENT DOCUMENTS

2014/0290652 A1* 10/2014 Davies ............... A61M 15/009
128/203.12

\* cited by examiner

ACTUATOR FOR A PACKAGE AND METHOD OF USE

TECHNICAL FIELD

The present invention relates generally to an apparatus or actuator for cooperatively working with a package containing a fluent substance to dispense the fluent substance from the package, typically in the form of a spray.

BACKGROUND OF THE INVENTION AND TECHNICAL PROBLEMS POSED BY THE PRIOR ART

Finger or hand-operable actuators are typically adapted to be incorporated in dispensing devices or systems mounted to, housing, or operatively engaged with containers storing a fluent substance or product. Some actuators are designed for use with a device having a suitable discharge structure or nozzle to produce a substance having desired properties or a desired consistency (e.g., such as an atomized spray, a foam, cream, etc.).

A dispensing package comprising such a nozzle and cooperating actuator is typically used for dispensing or dosing one or more medicaments in spray form, such as a rapid onset sublingual fentanyl spray, as well as other personal care or industrial products. SUBSYS® (SUBSYS is a registered trademark of and available from Insys Development Company, Inc.) is a commercially available rapid onset sublingual fentanyl spray covered by U.S. Pat. Nos. 8,486,972; 8,486,973; 8,835,459; 8,835,460; 9,241,935 and 9,289,387. "Sublingual" means "under the tongue" and refers to administration of a substance via the mouth in such a way that the substance is rapidly absorbed via the blood vessels under the tongue.

The SUBSYS® fentanyl spray is provided within and by a unit-dose spray package manufactured by Aptar Pharma, a subsidiary of AptarGroup, Inc., having principal offices at 475 W. Terra Cotta Ave., Suite E, Crystal Lake, Ill. The unit-dose spray package has a generally T-shaped body containing a sealed chamber with a predetermined unit-dose of the fluid medicament. The body is provided with a movable plunger extending within and from the body, which is slidably received therein, and which is located in confronting relationship with the sealed chamber. The body has an internal passageway terminating in a spray or exit orifice in the form of a nozzle for generating the SUBSYS® fentanyl spray when the plunger is sufficiently forced into the body by a user of the package to breach the sealed chamber. One or more frangible tabs, seals, or membranes initially prevents movement of the plunger relative to the body until the user accumulates a predetermined force on the plunger sufficient to rupture the frangible tabs.

The inventors have found that some users of such a package who are in a weakened state (e.g., those users having arthritis, undergoing cancer treatment, or suffering from other ailments affecting strength or coordination) may encounter difficulty in actuating and obtaining a proper unit-dose from the package. Specifically, it has been found by the inventors that such users may be unable to properly actuate the package by moving the plunger into the T-shaped body. Failure to breach the sealed chamber containing the unit-dose of a medicament in a fluid stroke could result in the failure to generate any unit dose of SUBSYS® fentanyl spray, or a failure to generate the full dose of fentanyl spray.

The inventors have recognized a need for an improved actuator and method for such weakened or arthritic users for effectively dispensing a unit-dose of a medicament from a package.

SUMMARY OF THE INVENTION

In accordance with one feature of the invention, an actuator is provided for operatively engaging and dispensing a fluent medicament from a package in the form of a spray. The package of the type having a body containing a fluent medicament, a plunger movable relative to the body, an internal flow passage terminating at an exit orifice, and a frangible member for initially preventing movement of the plunger relative to the body. The actuator including a housing with a recess configured to receive and hold the package. The actuator having a force amplification mechanism movably connected with the housing for receiving and amplifying an input force generated by a user of the actuator. The actuator further has a force transfer mechanism carried by the housing and configured to receive an amplified force from the force amplification mechanism and further configured to transmit the amplified force against the plunger of the package. The force amplification mechanism and the force transfer mechanism cooperatively arranged such that movement of the force amplification mechanism relative to the housing generates an amplified force against the plunger of the package sufficient to dispense the medicament from the exit orifice of the package in the form of a spray.

As one feature, the actuator is provided in combination with a package containing a fluent medicament. In one preferred feature, the fluent medicament is a sublingual fentanyl spray.

In one feature, the force amplification mechanism has the form of a lever arm.

According to another feature, the force transfer mechanism includes: a rod defining a first cam surface; and a gear having a plurality of teeth extending radially outwardly therefrom. The gear defines a second cam surface whereby movement of the first cam surface relative to the second cam surface causes the gear to rotate.

In another feature, the first cam surface has the form of a plurality of helical ribs extending along the length of the rod and the second cam surface has the form of a plurality of slots within a radially interior portion of the gear.

According to another feature, the rod is operatively connected to a first spring for returning the rod from an actuated position relative to the housing to an initial, unactuated position relative to the housing.

In another feature, the force transfer mechanism includes a piston having a plurality of teeth extending outwardly therefrom along a portion of the piston. The teeth of the piston are configured to be operatively engaged with the teeth of the gear.

According to another feature, the force transfer mechanism includes a drive spring operatively with the piston, the drive spring configured to accumulate force against the plunger of the package.

In another feature, the force transfer mechanism is arranged together with the force amplification mechanism so as to convert a substantially horizontal input force by the user of the actuator into a substantially vertical output force on the plunger of the package.

Other objects, features, and advantages of the invention will become apparent from a review of the entire specification, including the appended claims and drawings.

BRIEF DESCRIPTION OF THE DRAWINGS

FIG. 1 is an isometric view from the front and above of a hand-held, hand-operable actuator according to the invention, and FIG. 1 shows a unit-dose package installed within the actuator;

FIG. 2 is another isometric view of the front of the actuator of FIG. 1;

FIG. 3 is an isometric view of the rear of the actuator of FIG. 1;

FIG. 4 is an isometric view from the front of the actuator of FIG. 1, and FIG. 4 shows the unit-dose package removed from the actuator;

FIG. 8 is another enlarged, fragmentary view of the actuator in FIG. 4, and FIG. 8 shows a concealed drive spring in the force transfer mechanism;

FIG. 9 is a fragmentary view of a lower portion of the actuator of FIG. 1, and FIG. 9 shows the actuator in an initial, unactuated position;

FIG. 10 is an enlarged, fragmentary view of the actuator similar to FIG. 9, and FIG. 10 shows the actuator in an intermediate, actuated position;

FIG. 11 is an enlarged, fragmentary view of the actuator similar to FIG. 10, and FIG. 11 shows the actuator in an actuated, dispensing position;

FIG. 12 is an enlarged, fragmentary view of the actuator similar to FIG. 9, and FIG. 12 shows a concealed spring and the actuator in an initial, unactuated position;

FIG. 13 is an enlarged, fragmentary view similar to FIG. 10, and FIG. 13 shows compression of the concealed spring with the actuator in an intermediate, actuated position; and FIG. 14 is an enlarged, fragmentary view similar to FIG. 11, and FIG. 14 shows compression of the plunger of the unit-dose package with the actuator in an actuated, dispensing position.

DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, the components of this invention are described in a typical (upright) position, and terms such as upper, lower, horizontal, etc., are used with reference to this position. It will be understood, however, that the components embodying this invention may be manufactured, stored, transported, used, and sold in an orientation other than the position described.

Figures illustrating the components of this actuator invention and the package show some conventional mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

As will be further described in detail, the present invention is directed to an inventive actuator used to assist in the dispensing of a fluent medicament in a spray from a package.

FIGS. 1-14 illustrate an actuator according to the present invention designated by the numeral 200. FIGS. 1-3 and 9-14 illustrate a hand-held, finger-actuated package 100 of the type having a body 110 containing a fluent medicament (obstructed by the body 110), a plunger 120 movable relative to the body 110, an internal flow passage (obstructed by the body 110) terminating at an exit or spray orifice 130, and one or more frangible members (obstructed by the body 110) for initially preventing movement of the plunger 120 relative to the body 110.

The package 100 illustrated is a SUBSYS® fentanyl spray is available from Insys Development Company, Inc., which is provided within a unit-dose spray container manufactured by Aptar Pharma, a subsidiary of AptarGroup, Inc., having principal offices at 475 W. Terra Cotta Ave., Suite E, Crystal Lake, Ill. (the container and medicament together constituting the "package"). The detailed design and construction of the package 100 per se forms no part of the present invention. It should further be understood that while the preferred embodiment of the actuator 200 is shown herein for use with the illustrated package 100, in some applications it may be desirable to utilize an actuator 200 according to the invention with other types of packages or containers of other medicaments, industrial products, or fluent substances in general.

Figures 1, 2:
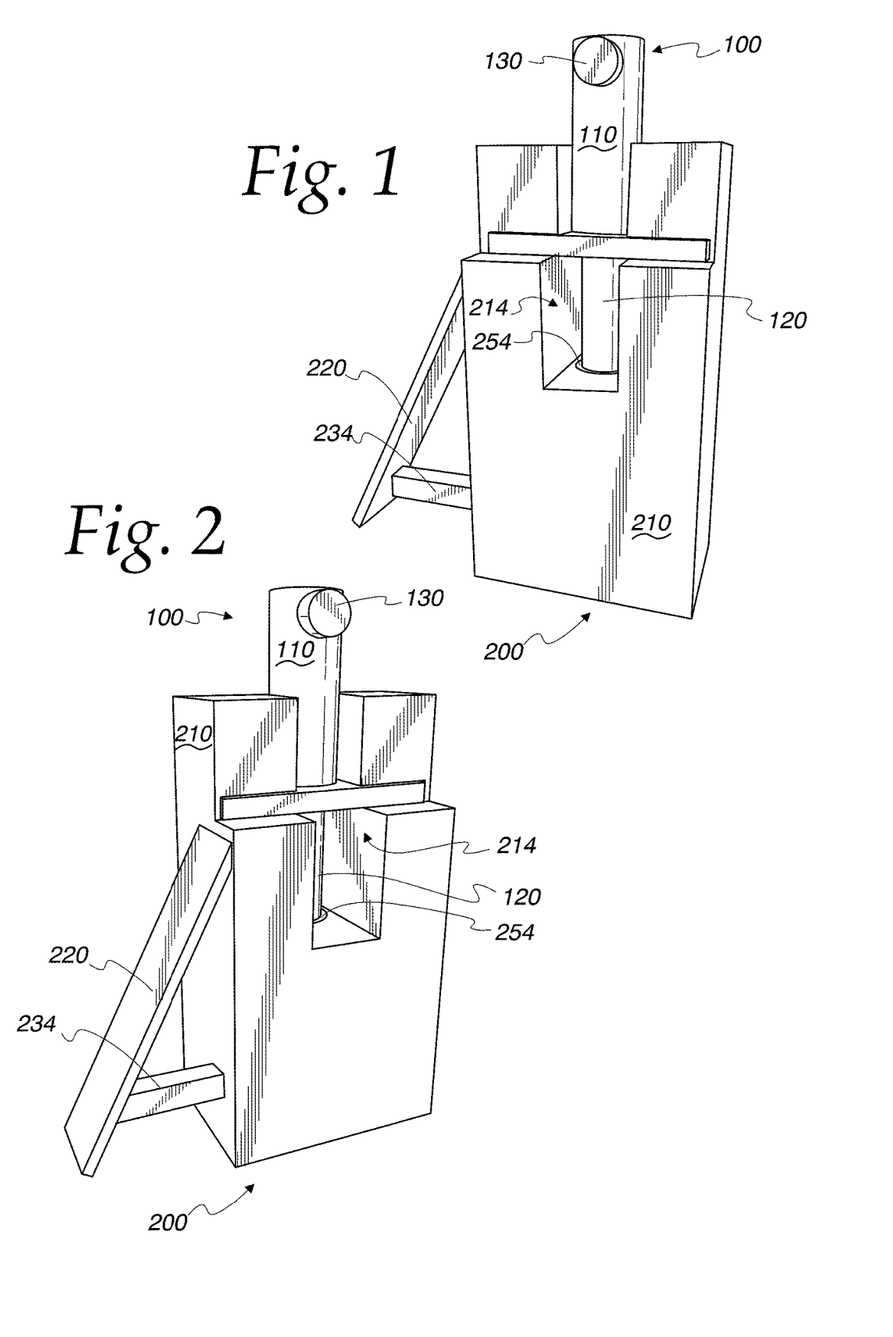

With reference now to FIG. 2, the actuator 200 has a housing 210 with a dock or recess 214 sized and shaped to receive and hold the package 100. While the housing 210 is shown in a generic block form, and it will be appreciated that it may have a different shape other than the one shape shown (e.g., with rounded corners or surfaces, polygonal portions, or an overall amorphous shape, etc.).

Figures 3, 4:
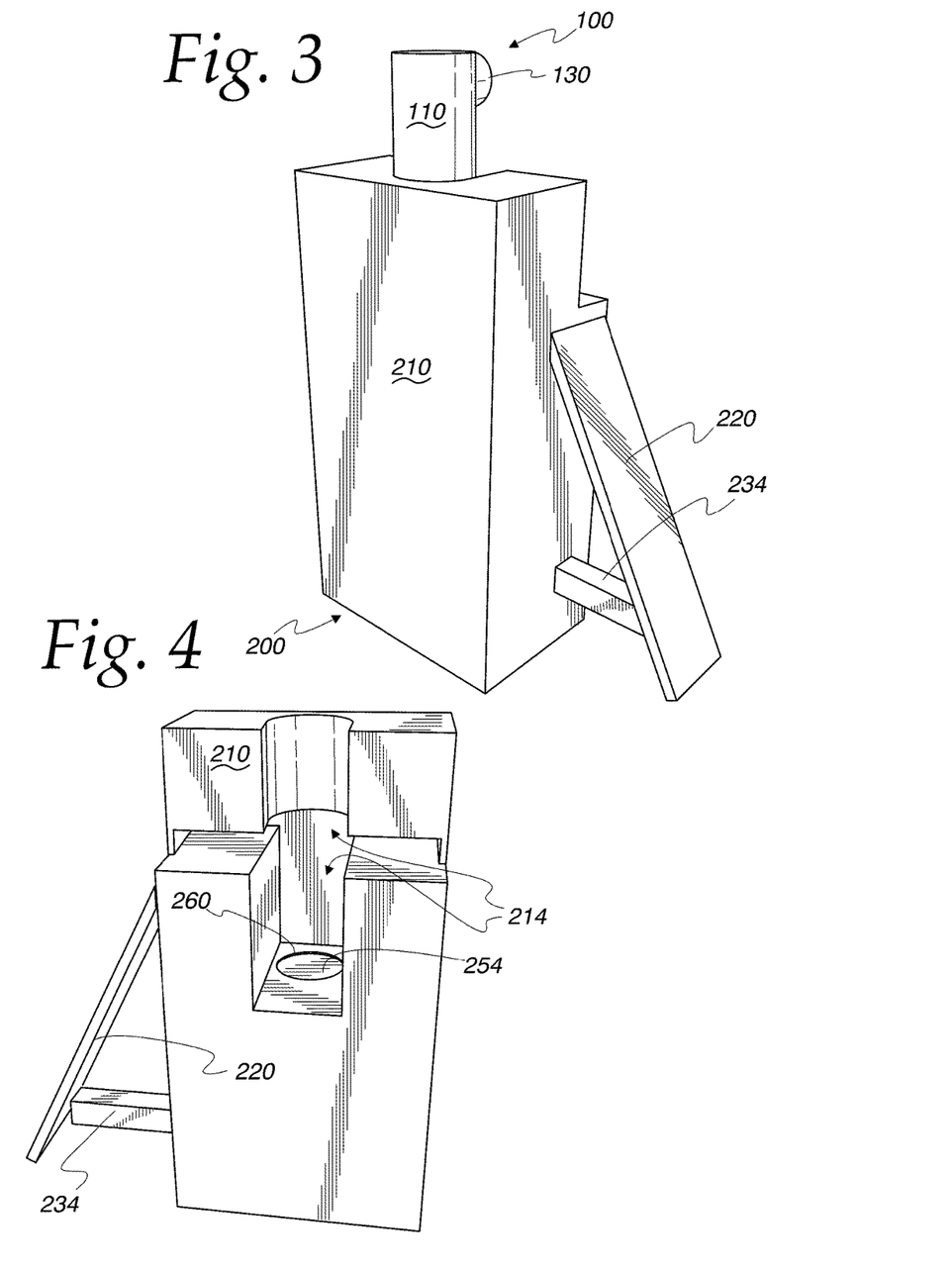
Figure 5:
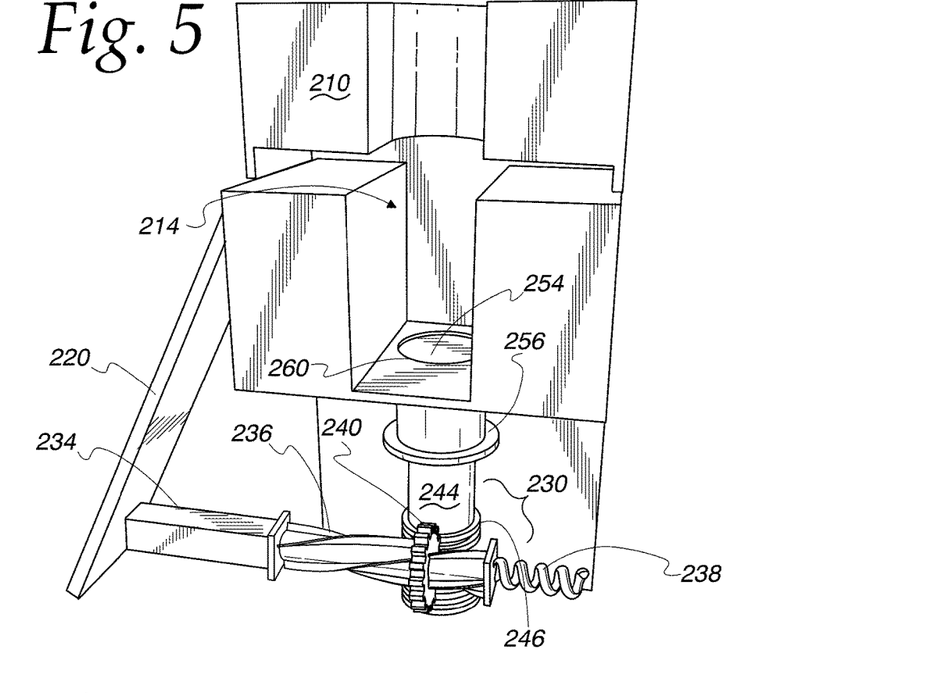
FIG. 5 is a fragmentary view of the actuator of FIG. 4 showing the force transfer mechanism within the actuator.

With reference now to FIGS. 2, 3, and 5, the actuator 200 is provided with a force amplification mechanism 220 that is movably connected with the housing 210 for receiving and amplifying an input force generated by a user of the actuator 200. In the embodiment of the actuator 200 illustrated, the force amplification mechanism 220 has the form of a lever arm connected with housing 210. It will be understood by one of ordinary skill in the art that other force amplification mechanisms might be used, such as a compound lever, gear train, pulley, crank, etc. to effectuate a reduction of the user input force required to ultimately evacuate a spray of a unit-dose from the package 100. Furthermore, it may not be necessary that the amplification mechanism 220 actually amplify the input force of the user, and may instead function to distribute the force required to dispense a fluent substance from the package 100 across the fingers and/or hand of the user.

Figure 6:
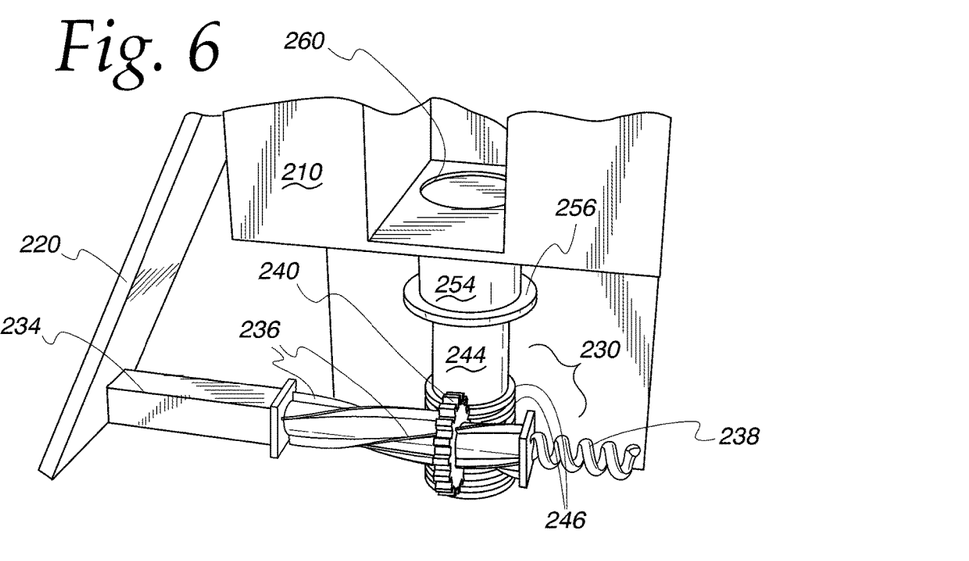
FIG. 6 is an enlarged, fragmentary view of the actuator similar to FIG. 5.
Figure 7:
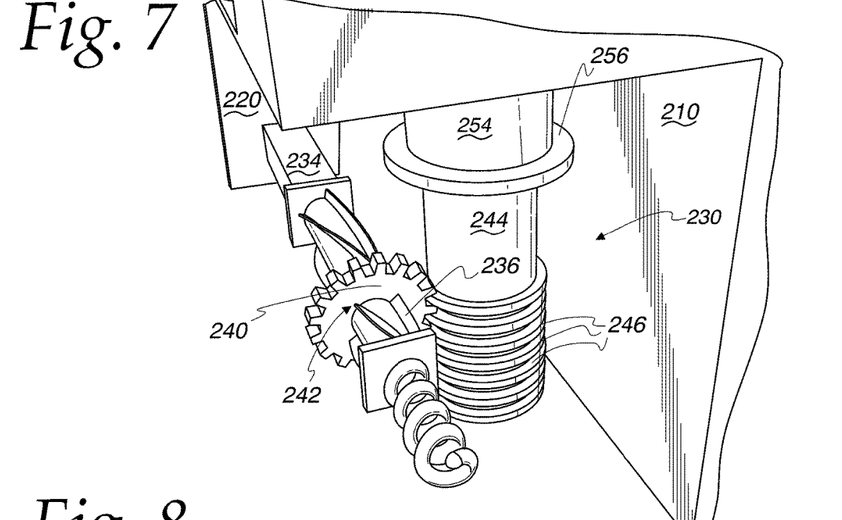
FIG. 7 is another enlarged, fragmentary view of the actuator in FIG. 4.
Figure 8:
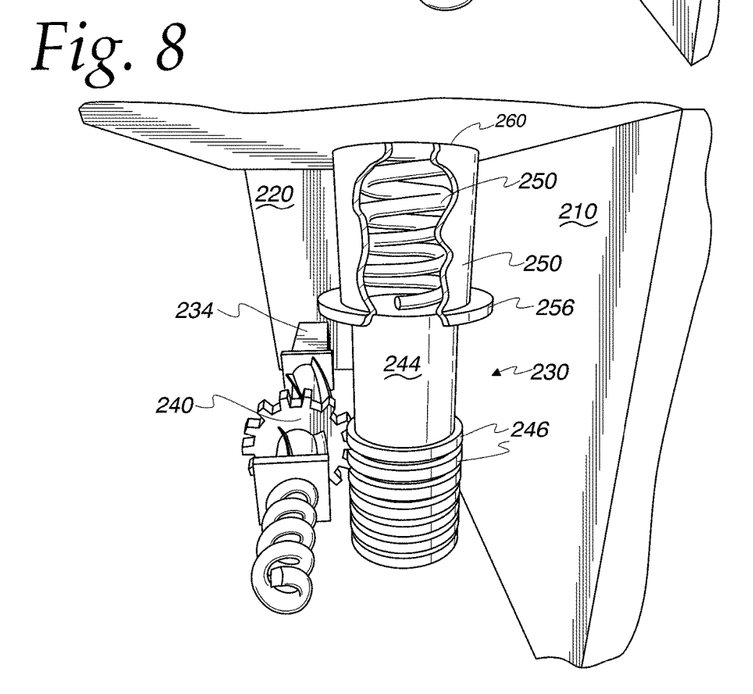

Referring now to FIGS. 5 and 6, one end of the lever arm is hingedly connected with the housing 210 and the other end of the lever arm is connected to a force transfer mechanism 230. The force transfer mechanism 230 is located partially within and carried by the housing 210 and is configured to receive an amplified force from the lever arm. The force transfer mechanism 230 is further configured to transmit the amplified force against the plunger 120 of the package 100, as shown in FIGS. 9-14. Movement of the lever arm, or other force amplification mechanism 220, relative to the housing 210 generates a force against the plunger 120 of the package 100 sufficient to dispense the medicament from the spray orifice 130 of the package 100 in the form of a spray.

Figure 9:
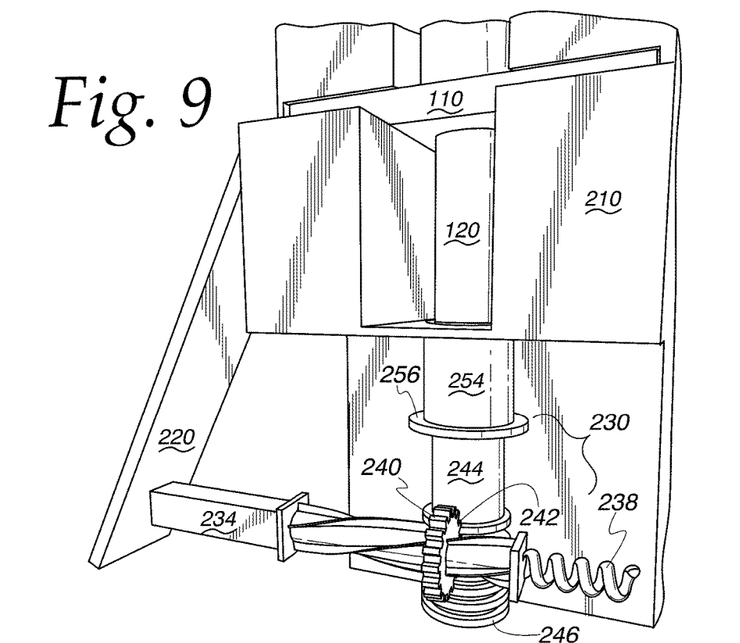
Figure 10:
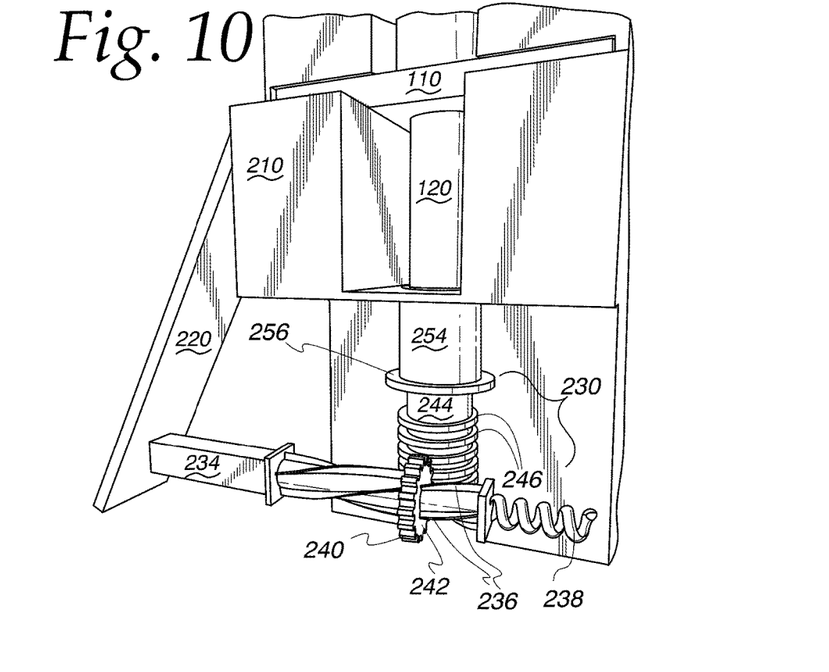

Referring now to FIGS. 9 and 10, as previously discussed above, one end of the lever arm is hingedly connected with the housing 210. The other, distal end of the lever arm is operably connected with, or abutting, a rod 234 component of the force transfer mechanism 230. The rod 234 defines a first cam surface in the form of a plurality of helical protrusions or ribs 236 extending along the length of the rod 234. A return spring 238 is retained within the housing 210 and is positioned at the distal end of the rod 234 for returning or translating the rod 234 from an actuated position relative to the housing 210 to an initial, unactuated position relative to the housing 210, which will be discussed in greater detail below with respect to the operation of the actuator 200.

Still referring to FIGS. 9 and 10, the rod 234 passes through a pinion or gear 240 that is retained in the housing 210. The gear 240 is a spur gear having a plurality of teeth extending radially outwardly therefrom. The internal surface of the gear 240 defines a second cam surface in the form of four slots 242, each one of which receives one of the ribs 236 of the rod 234. Movement of the first cam surface relative to the second cam surface, via translation of the rod 234 through the gear 240, forces the gear 240 to rotate. The teeth of the gear 240 are engaged with a piston 244 having a plurality of axially-spaced concentric ribs or teeth 246 that collectively form a rack. Engagement of the teeth of the gear 240 together with the rack carried on the piston 244, together with rotation of the gear 240 in a first direction, causes the piston 244 to translate vertically upwards within the housing 210 (compare FIGS. 9 and 10, and compare FIGS. 12 and 13). It will be appreciated that other suitable gear types may be used, such as a helical rack and pinion, etc.

Figures 11, 12:
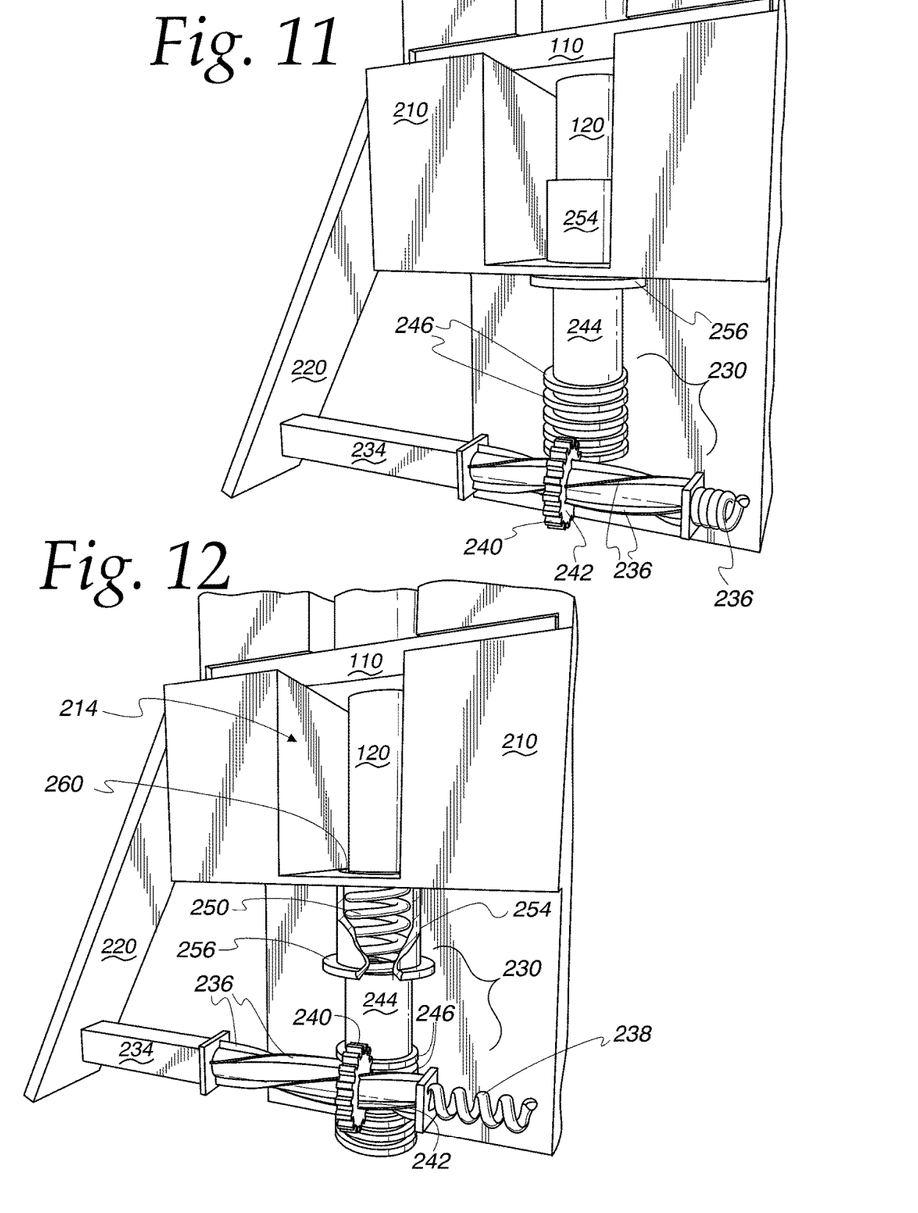
Figures 13, 14:
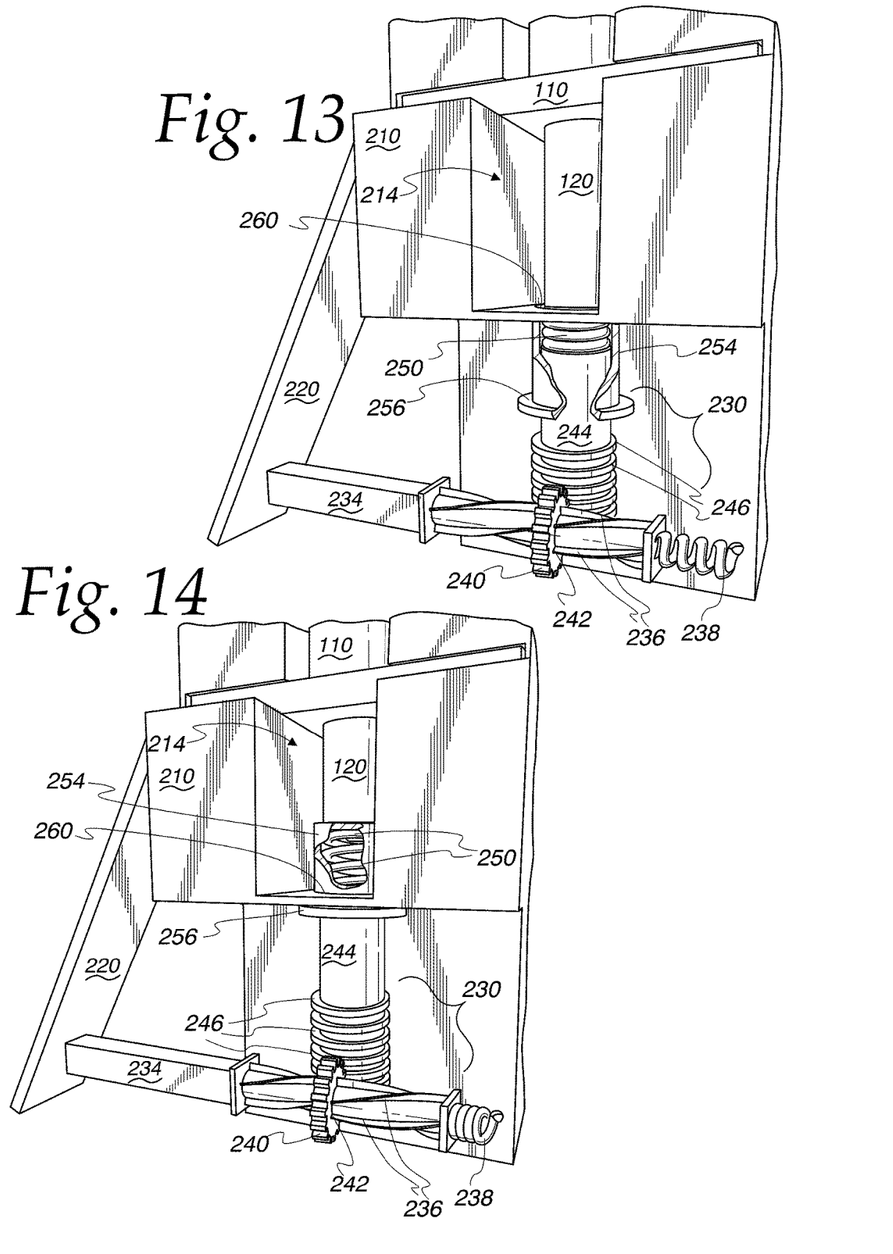

Referring now to FIGS. 12 and 13, a distal end of the cylindrical piston 244 abuts a drive spring 250 that is retained within a cup-shaped carrier member 254, which has an open, proximal end for receiving the piston 244 and a closed, distal end against which the drive spring 250 rests. The carrier member 254 has an annular flange 256 and an outer cylindrical wall that is slidably disposed within an aperture 260 in the housing 210. Interference between the flange 256 and a portion of the housing 210 that surrounds the aperture 260 prevents the carrier member 254 from completely passing through the aperture 260 as the carrier member 254 slides vertically relative to the housing 210. As will be discussed in greater detail hereinafter, the translation of the piston 244 vertically upwards against the drive spring 250 accumulates force between the closed end of the carrier member 254 and the plunger 120 of the package 100.

While force transfer mechanism 230 illustrated is shown with specific components of a rifled rod 234, a gear 240, a piston 244 having a rack, a return spring 238, a drive spring 250, and a carrier member 254, it will be appreciated that the force transfer mechanism 230 need not be limited to such components and may be formed from other suitable mechanical alternatives arranged together so as to convert a substantially horizontal input force on the force amplification mechanism into a substantially vertical output force on the plunger 120 of the package 100 sufficient to dispense the medicament from the package 100.

In another embodiment of the present invention (not illustrated), the aforementioned internal gear train within the housing 210 may be replaced by a linear electric actuator, such as a solenoid or linear motor, for driving the piston 244 vertically within the housing 210 into the carrier member 254.

In still another embodiment of the present invention (not illustrated), a rotational electric motor may be positioned within the housing 210 to drive the piston 244 vertically within the housing 210 into the carrier member 254, thus replacing the gear 240.

Operation of the actuator 200 in combination with the package 100 will now be discussed. Initially, the package 100 is loaded into the recess 214 of the actuator housing 210 by a user. As can be seen in FIGS. 1-2, the package 100 is oriented such that the plunger 120 is located adjacent to, or abutting, the carrier member 254 while the spray orifice 130 of the package 100 extends free and clear of the housing 210. The body 110 of the package is restrained in this position. A locking tab, detent, frictional engagement, or other securing means (not illustrated) could be used to temporarily secure the package 100 within the housing 210.

With the package 100 loaded into the actuator 200, a user would grip the housing 210 to orient the spray orifice 130 proximal to the underside of the user's tongue such that a unit-dose of medicament in spray form would exit from the spray orifice 130 to be effectively absorbed under the user's tongue. With the loaded actuator 200 in the initial, unactuated position shown in FIGS. 5-9, the user would then compress the force amplification mechanism 220 with the fingers of one hand, while simultaneously gripping the housing 210 with the thumb of the same hand. In this manner, the lever rotates about the hinged connection with the housing 210 such that the lever drives the rod 234 inward into the housing 210. The helical ribs 236, extending along the length of the rod 234, slide through the slots 242 of the gear 240 and force the gear 240 to rotate based on the curved path defined by the helical ribs 236. The gear 240 is otherwise prevented from translating together with the rod 234 by the housing 210. The return spring 238 is compressed within the housing 210 as shown in FIGS. 10 and 11 as the rod 234 is pressed inward.

With reference to FIGS. 9-11, the rotation of the gear 240 engages the rack of the piston 244 to drive the piston 244 upwards within the housing 210. Referring now to FIGS. 12-14, it can be seen that the upwards movement of the piston 244 compresses the drive spring 250 against the closed end of the carrier member 254. As the gear 240 continues to drive the piston 244 upwards, as a result of the user driving the rod 234 further into the housing, the force of the carrier member 254 against the plunger 120 increases until the frangible members (obstructed by the body 110) are broken away, to allow the plunger 120 to move relative to the body 110. With the frangible members overcome within the package 100, the carrier member 254 travels upward through the aperture 260 a predetermined stroke length, limited only by the annular flange 256 of the carrier member 254 abutting the housing 210 surrounding the aperture 260.

Movement of the plunger 120 into the body 110 of the package 100 forces the unit-dose of the medicament through an internal flow passage of the body 110 and through the spray orifice 130 to the target location beneath the user's tongue.

The user subsequently releases the lever, allowing for decompression of the return spring 238 to translate the rod 234 from the actuated position relative to the housing 210 back to the initial, unactuated position relative to the housing 210. Return of the rod 234 through the gear 240 causes the helical ribs 236 of the rod 234 to rotate the gear 240 in a second, opposite direction. Rotation of the gear 240 in this opposite direction forces the piston 244 downwards within the housing 210 and allows the drive spring 250 and carrier member 254 to return to the initial, unactuated position for subsequent reuse.

The inventors have discovered that providing the actuator 200 with a force amplification mechanism 220 and force transfer mechanism 230 allows for a user to dispense a medicament spray from the package 100 with less force required from each finger of the user. The inventors have found that this advantage can be critical for some users suffering from muscle weakness or joint pain.

In yet another embodiment of the present invention (not illustrated), one or more movable blocking members may be positioned between carrier member 254 and the plunger 120. The blocking members are positioned to cover the aperture 260 such that carrier member 254 is prevented from moving upward against the plunger 120. In this manner, the piston 244 can compress the drive spring 250 until a predetermined potential energy is stored within the spring 250. The blocking members are then actuated by spring or electrical mechanism to move out of the position between the carrier member 254 and the plunger 120. Preferably, the blocking members have the form of a pair of flat plates that meet substantially in the middle of, and just below, the aperture 260.

Storing a sufficient amount of potential energy in the drive spring 250, prior to movement of the carrier member 254 against the plunger 120, ensures that there is a sufficient force generated to break the internal tabs in the package 100 to dispense a suitable dose of fluent medication.

What is claimed is:

1. An actuator for operatively engaging and dispensing a fluent medicament from a package in the form of a spray, said package of the type having a body containing a fluent medicament, a plunger movable relative to the body, an internal flow passage terminating at an exit orifice, and a frangible member for initially preventing movement of the plunger relative to the body, said actuator comprising:
   a housing with a recess configured to receive and hold the package;
   a force amplification mechanism movably connected with the housing for receiving and amplifying an input force generated by a user of the actuator; and
   a force transfer mechanism carried by the housing and configured to receive an amplified force from the force amplification mechanism, the force transfer mechanism further configured to transmit the amplified force against the plunger of the package,
wherein movement of the force amplification mechanism relative to the housing generates an amplified force against the plunger of the package sufficient to dispense the medicament from the exit orifice of the package in the form of a spray and wherein the force transfer mechanism includes: a rod defining a first cam surface; and a gear having a plurality of teeth extending radially outwardly therefrom, the gear defining a second cam surface, wherein movement of the first cam surface relative to the second cam surface causes the gear to rotate and wherein the force transfer mechanism includes a piston having a plurality of teeth extending outwardly therefrom along a portion of the piston, the teeth of the piston operatively engaged with the teeth of the gear.

2. The actuator of claim 1 in combination with a package containing a fluent medicament.

3. The combination of an actuator and a package of claim 2 wherein the medicament is a sublingual fentanyl spray.

4. The actuator of claim 1 wherein the force amplification mechanism has the form of a lever arm.

5. The actuator of claim 1 wherein the first cam surface has the form of a plurality of helical ribs extending along the length of the rod, and the second cam surface has the form of a plurality of slots within a radially interior portion of the gear.

6. The actuator of claim 1 wherein the rod is operatively connected to a return spring for returning the rod from an actuated position relative to the housing to an initial, unactuated position relative to the housing.

7. The actuator of claim 1 wherein the force transfer mechanism includes a piston having a plurality of teeth extending outwardly therefrom along a portion of a length of the piston, the teeth of the piston operatively engaged with the teeth of the gear.

8. The actuator of claim 7 wherein the force transfer mechanism includes a drive spring operatively engaged by the piston, the drive spring configured to accumulate force against the plunger of the package.

9. The actuator of claim 1 wherein the force transfer mechanism is arranged together with the force amplification mechanism so as to convert a substantially horizontal input force on the force amplification mechanism into a substantially vertical output force on the plunger of the package.

10. A method of using an actuator for operatively engaging and dispensing a fluent medicament from a package in the form of a spray, the method comprising the steps of:
   obtaining an actuator according to claim 1;
   installing a package within the actuator, the package of the type having a body containing a fluent medicament, a plunger movable relative to the body, an internal flow passage terminating at an exit orifice, and a frangible member for initially preventing movement of the plunger relative to the body;
   gripping the housing of the actuator in one hand to generate an input force on the force amplification mechanism; and
   amplifying and transferring the input force against the plunger of the package sufficient to dispense the medicament from the exit orifice of the package in the form of a spray.

* * * * *